(12) United States Patent
Wennerbäck (10) Patent No.: US 9,102,132 B2
(45) Date of Patent: Aug. 11, 2015

(54) ABSORBENT ARTICLE COMPRISING AN ELASTIC LAMINATE MATERIAL

(75) Inventor: Margareta Wennerbäck, Mölnlycke (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 859 days.

(21) Appl. No.: 12/514,086

(22) PCT Filed: Nov. 13, 2006

(86) PCT No.: PCT/SE2006/001284
§ 371 (c)(1),
(2), (4) Date: May 8, 2009

(87) PCT Pub. No.: WO2008/060194
PCT Pub. Date: May 22, 2008

(65) Prior Publication Data
US 2009/0306616 A1    Dec. 10, 2009

(51) Int. Cl.
*A61F 13/15* (2006.01)
*B32B 37/20* (2006.01)
(Continued)

(52) U.S. Cl.
CPC ......... *B32B 37/203* (2013.01); *A61F 13/15203* (2013.01); *A61F 13/4902* (2013.01);
(Continued)

(58) Field of Classification Search
CPC ........... A61F 13/15203; A61F 13/4902; A61F 13/511; A61F 13/51458; A61F 13/51464; A61F 13/51478; A61F 2013/15292; B32B 2305/20; B32B 2307/51; B32B 2309/14; B32B 2555/02; B32B 37/203

USPC .......................................................... 604/367
See application file for complete search history.

(56) References Cited

U.S. PATENT DOCUMENTS 3,259,539 A   7/1966   Katz et al.
3,424,162 A   1/1969   Parravicini
(Continued)

FOREIGN PATENT DOCUMENTS

CO   2007-0003796   1/2008
EP   0 287 388 A2   10/1988
(Continued)

OTHER PUBLICATIONS

An English Translation of the Notice of Reasons for Rejection issued in the corresponding Japanese Patent Application No. 2007-517994 dated Nov. 24, 2009.
(Continued)

*Primary Examiner* — Lynne Anderson
*Assistant Examiner* — Bradley Philips
(74) *Attorney, Agent, or Firm* — Buchanan Ingersoll & Rooney PC (57) ABSTRACT

A pant type absorbent article having a core region includes an absorbent core and a chassis region surrounding the core region. The article in at least a part of the chassis region includes a coversheet in the form of an elastic laminate constituting the sole component of the chassis in at least 20% of the total surface area of the article. The elastic laminate has a tensile strength of at least 15 N/25 mm both in the longitudinal and transverse directions of the article and a tensile strength in the transverse direction of the article which is no more than 2.5 times and preferably no more than 2 times higher than the tensile strength in the longitudinal direction of the article. The force required to extend the elastic laminate 10% in the longitudinal direction of the article is no more than 5 N/25 mm.

36 Claims, 4 Drawing Sheets

(51) Int. Cl.
*A61F 13/511* (2006.01)
*A61F 13/514* (2006.01)
*A61F 13/49* (2006.01)

(52) U.S. Cl.
CPC ......... *A61F13/511* (2013.01); *A61F 13/51458* (2013.01); *A61F 13/51464* (2013.01); *A61F 13/51478* (2013.01); *A61F 2013/15292* (2013.01); *A61F 2013/49022* (2013.01); *A61F 2013/49057* (2013.01); *B32B 2305/20* (2013.01); *B32B 2307/51* (2013.01); *B32B 2309/14* (2013.01); *B32B 2555/02* (2013.01)

(56) References Cited

U.S. PATENT DOCUMENTS

| | | |
|---|---|---|
| 4,119,450 A | 10/1978 | Bianco |
| 4,663,220 A | 5/1987 | Wisneski et al. |
| 4,698,261 A | 10/1987 | Bothe et al. |
| 4,739,012 A | 4/1988 | Hagman |
| 4,777,080 A | 10/1988 | Harris, Jr. et al. |
| 4,842,596 A | 6/1989 | Kielpikowski et al. |
| 4,850,990 A | 7/1989 | Huntoon et al. |
| 4,932,949 A | 6/1990 | Thygesen et al. |
| 5,114,781 A | 5/1992 | Morman |
| 5,143,679 A | 9/1992 | Weber et al. |
| 5,156,793 A | 10/1992 | Buell et al. |
| 5,167,897 A * | 12/1992 | Weber et al. ............. 264/288.8 |
| 5,261,899 A | 11/1993 | Visscher et al. |
| 5,336,545 A | 8/1994 | Morman |
| 5,422,172 A | 6/1995 | Wu |
| 5,440,764 A | 8/1995 | Matsushita |
| 5,462,541 A | 10/1995 | Bruemmer et al. |
| 5,514,470 A | 5/1996 | Haffner et al. |
| 5,592,690 A | 1/1997 | Wu |
| 5,628,738 A | 5/1997 | Suekane |
| 5,634,216 A | 6/1997 | Wu |
| 5,635,290 A | 6/1997 | Stopper et al. |
| 5,706,524 A | 1/1998 | Herrin et al. |
| 5,733,628 A | 3/1998 | Pelkie |
| 5,746,730 A | 5/1998 | Suzuki et al. |
| 5,769,838 A | 6/1998 | Buell et al. |
| 5,861,074 A * | 1/1999 | Wu ............................. 156/229 |
| 5,921,973 A | 7/1999 | Newkirk et al. |
| 6,072,005 A | 6/2000 | Kobylivker et al. |
| 6,106,925 A | 8/2000 | Palumbo |
| 6,210,386 B1 | 4/2001 | Inoue |
| 6,240,569 B1 | 6/2001 | Van Gompel et al. |
| 6,476,289 B1 | 11/2002 | Buell et al. |
| 6,540,731 B2 | 4/2003 | Magnusson et al. |
| 6,552,245 B1 | 4/2003 | Roessler et al. |
| 6,585,713 B1 * | 7/2003 | LeMahieu et al. ........... 604/392 |
| 6,627,564 B1 | 9/2003 | Morman et al. |
| 6,914,018 B1 | 7/2005 | Uitenbroek et al. |
| 7,211,531 B2 * | 5/2007 | Schneider et al. ........... 442/328 |
| 7,320,948 B2 * | 1/2008 | Morman et al. ............. 442/394 |
| 7,722,591 B2 | 5/2010 | Back |
| 7,824,389 B2 * | 11/2010 | Veith ....................... 604/385.23 |
| 8,298,205 B2 * | 10/2012 | Norrby et al. ............ 604/385.24 |
| 2002/0002021 A1 | 1/2002 | May et al. |
| 2002/0004350 A1 | 1/2002 | Morman et al. |
| 2002/0019187 A1 | 2/2002 | Carroll et al. |
| 2002/0029026 A1 | 3/2002 | Furuya et al. |
| 2002/0052591 A1 | 5/2002 | Zehner et al. |
| 2003/0022582 A1 | 1/2003 | Cree et al. |
| 2003/0078558 A1 | 4/2003 | Karami et al. |
| 2003/0088230 A1 | 5/2003 | Balogh et al. |
| 2003/0091807 A1 * | 5/2003 | Desai et al. ................. 428/297.4 |
| 2003/0105446 A1 * | 6/2003 | Hutson et al. ............. 604/385.22 |
| 2003/0124310 A1 | 7/2003 | Ellis et al. |
| 2003/0135184 A1 | 7/2003 | Van Gompel et al. |
| 2004/0073188 A1 * | 4/2004 | Mitsui et al. .................. 604/391 |
| 2004/0078018 A1 | 4/2004 | Van Gompel et al. |
| 2004/0087235 A1 * | 5/2004 | Morman et al. ............. 442/394 |
| 2004/0102746 A1 | 5/2004 | Mortell et al. |
| 2004/0116887 A1 | 6/2004 | Thorson et al. |
| 2004/0122405 A1 | 6/2004 | Van Gompel et al. |
| 2004/0122406 A1 | 6/2004 | Moser et al. |
| 2004/0127878 A1 | 7/2004 | Olson et al. |
| 2004/0133180 A1 | 7/2004 | Mori et al. |
| 2004/0192140 A1 | 9/2004 | Schneider et al. |
| 2004/0197588 A1 | 10/2004 | Thomas et al. |
| 2004/0241389 A1 | 12/2004 | Chung et al. |
| 2004/0243086 A1 | 12/2004 | Van Gompel et al. |
| 2005/0010186 A1 | 1/2005 | Otsubo et al. |
| 2005/0101216 A1 | 5/2005 | Middlesworth et al. |
| 2005/0106980 A1 | 5/2005 | Abed et al. |
| 2006/0148358 A1 | 7/2006 | Hall et al. |
| 2007/0233034 A1 | 10/2007 | Hildeberg et al. |
| 2008/0000003 A1 | 1/2008 | Melander |
| 2008/0033387 A1 | 2/2008 | Wastlund-Karlson et al. |
| 2009/0221982 A1 * | 9/2009 | Cecconi et al. ............ 604/385.3 |

FOREIGN PATENT DOCUMENTS

| | | |
|---|---|---|
| EP | 0 304 957 A2 | 3/1989 |
| EP | 0 360 929 A1 | 4/1990 |
| EP | 0 409 307 B1 | 1/1991 |
| EP | 0 418 493 A1 | 3/1991 |
| EP | 0 486 006 B1 | 9/1996 |
| EP | 0 861 647 A2 | 9/1998 |
| EP | 0 714 351 B1 | 12/1998 |
| EP | 0 605 012 B1 | 3/1999 |
| EP | 0 604 731 B1 | 6/1999 |
| EP | 1 035 818 A1 | 9/2000 |
| EP | 1 184 022 A2 | 3/2002 |
| EP | 1 384 459 A2 | 7/2003 |
| EP | 1 473 008 A1 | 11/2004 |
| FR | 2 586 558 | 3/1987 |
| FR | 2 810 879 | 1/2002 |
| GB | 2 284 538 A | 6/1995 |
| JP | 06255006 A | 9/1994 |
| JP | 07-252762 | 10/1995 |
| JP | 9-286085 A | 11/1997 |
| JP | 10-043235 A | 2/1998 |
| JP | 2002 058 703 A | 2/2002 |
| JP | 2002-65740 A | 3/2002 |
| JP | 2002-172137 A | 6/2002 |
| JP | 2002-520090 T | 7/2002 |
| JP | 2002-273808 | 9/2002 |
| JP | 2003-520146 | 7/2003 |
| JP | 2003-290284 A | 10/2003 |
| JP | 2004-050621 | 2/2004 |
| JP | 2004-098356 A | 4/2004 |
| JP | 2004-519270 | 7/2004 |
| RU | 2 008 774 | 3/1994 |
| RU | 2 221 531 | 1/2004 |
| SU | 965339 | 10/1982 |
| SU | 965339 A3 | 10/1982 |
| TW | 233473 | 11/1994 |
| WO | WO 95/19258 | 7/1995 |
| WO | WO 96/10979 A1 | 4/1996 |
| WO | WO 97/29722 A1 | 8/1997 |
| WO | WO 97/34037 A1 | 9/1997 |
| WO | WO 98/37847 A1 | 9/1998 |
| WO | WO 99/27876 A1 | 6/1999 |
| WO | WO 99/32164 A1 | 7/1999 |
| WO | WO 00/02511 A1 | 1/2000 |
| WO | WO 00/45764 A1 | 8/2000 |
| WO | WO 01/30563 A1 | 5/2001 |
| WO | WO 01/45927 A1 | 6/2001 |
| WO | WO 01/53076 | 7/2001 |
| WO | WO 02/34185 | 5/2002 |
| WO | WO 02/49560 A1 | 6/2002 |
| WO | WO 03/004748 A1 | 1/2003 |
| WO | WO 03/019714 A1 | 3/2003 |
| WO | WO 03/047488 A1 | 6/2003 |
| WO | WO 2004/058120 A1 | 7/2004 |
| WO | WO 2004/060251 A1 | 7/2004 |
| WO | WO 2004/078083 A1 | 9/2004 |
| WO | WO 2005/122984 A1 | 12/2004 |
| WO | WO 2005/095700 A1 | 10/2005 |
| WO | WO 2005/122985 A1 | 12/2005 |
| WO | WO 2006/038837 A1 | 4/2006 |

(56) References Cited

FOREIGN PATENT DOCUMENTS

| WO | WO 2006/093439 A1 | 9/2006 |
|----|----|----|
| WO | WO 2006/093440 A1 | 9/2006 |
| WO | WO 2006/093443 A1 | 9/2006 |
| WO | WO 2007/114744 A1 | 10/2007 |
| WO | WO 2008/060194 A1 | 5/2008 |

OTHER PUBLICATIONS

Official Action issued on Jul. 26, 2011 in U.S. Appl. No. 11/576,497.
Form PCT/ISA/210 (International Search Report) dated Jun. 29, 2007.
Form PCT/ISA/237 (Written Opinion of the International Searching Authority) dated Jun. 29, 2007.
Hildeberg et. al, Copending U.S. Appl. No. 11/630,371, filed Dec. 21, 2006 entitled "Absorbent Article Comprising an Elastic Laminate Material".
Karlson et al., Copending U.S. Appl. No. 11/576,497, filed Dec. 3, 2008 entitled "Absorbent Article Comprising an Elastic Web Material".
Wastlund-Karlssson et al., Copending U.S. Appl. No. 11/630,372, filed Dec. 21, 2006 entitled "Absorbent Article Comprising an Elastic Laminate".
Melander, Copending U.S. Appl. No. 11/845,153, filed Aug. 27, 2007 entitled "Underwear Article Comprising an Elastic Laminate".
Wennerback, Copending U.S. Appl. No. 12/446,297, filed Apr. 20, 2009 entitled "Absorbent Article Comprising an Elastic Laminate".
Norrby et al., Copending U.S. Appl. No. 12/447,694, filed Apr. 29, 2009 entitled "Elastic Laminate and Absorbent Article Comprising the Laminate".
Non-Final Office Action in Copending U.S. Appl. No. 11/630,372 to Wastlund-Karlson et al. dated Sep. 16, 2009.
Final Office Action in Copending U.S. Appl. No. 11/630,372 to Wastlund-Karlson et al. dated Mar. 2, 2008.
Non-Final Office Action in Copending U.S. Appl. No. 11/630,372 to Wastlund-Karlson et al. dated Jul. 8, 2009.
Non-Final Office Action in Copending U.S. Appl. No. 11/630,371 to Hildeberg et al. dated Oct. 5, 2009.
Sueo Kawabata, "The Standardization and Analysis of Hand Evaluation", Second Edition, The Hand Evaluation and Standardization Committee, The Textile Machinery Society of Japan, published by the Textile Machinery Society of Japan, Osaka, Japan, Jul. 1980—Textile Machinery Japan.

* cited by examiner

ABSORBENT ARTICLE COMPRISING AN ELASTIC LAMINATE MATERIAL

TECHNICAL FIELD

The present invention refers to a pant type absorbent article such as a pant diaper, a sanitary pant or incontinence garment, said article comprising an elastic laminate material.

BACKGROUND OF THE INVENTION

Absorbent articles having defined core regions and chassis regions are supposed to have a comfortable fit about the wearer. For pant articles like pant diapers, sanitary pants and incontinence pants it is also desirable that the articles are capable of being pulled up and down over the hips of the wearer to allow the wearer or caregiver to easily put on and remove the article when it has been soiled. It is known to make such absorbent pants with elasticized stretchable side panels and waist portion, usually comprising elastic members, such as elastic threads, contractably affixed between the backsheet and the topsheet.

It is further known to make portions of the chassis of absorbent articles of an elastic material, such as stretch-bonded laminates. Such laminates may include a layer of meltblown elastomeric fibers which have been stretched and sandwiched between outer layers of spunbonded webs.

U.S. Pat. No. 6,552,245 discloses an extensible outer cover for an absorbent article which provides a certain permanent deformation when subjected to a tensile force. The extensible outer cover comprises a necked laminate in the form of one layer of a necked non-elastic film and one layer of an elastic film. The films may be breathable.

WO 03/047488 discloses an elastic laminate comprising an elastic film which on opposite sides is bonded to first and second non-elastic fibrous layers. The laminate is made by bonding the non-elastic fibrous layers to the elastic film layer and subsequently stretching the composite material, causing the non-elastic materials to break. The elastic film material may be of a breathable material. The laminate may be incorporated in an absorbent article.

US2003/0022582 describes a laminate in which an elastomeric film is bound between two or more layers of nonwoven webs. The laminate is said to be particularly useful in elastic diaper "ears" that can be stretched to accommodate variously sized wearers.

U.S. Pat. No. 6,627,564 discloses a laminate which is elastic in a machine direction and extendable but not elastic in a cross direction. The laminate comprises a nonwoven web that is extendible in cross direction and a plurality of elastic members laminated to the web, said elastic members are elongatable in the machine direction and bonded to the nonwoven web in space apart location while in a stretched condition. The laminate may be used as an outer cover in personal care absorbent articles.

Further examples of absorbent articles which in part are made of elastic laminates are found in U.S. Pat. No. 6,476,289 and JP 10043235.

International applications PCT/SE2004/001004 and PCT/SE2004/001005 refer to absorbent articles comprising an outer coversheet in the form of an elastic laminate having improved cloth-like feel and puncture resistance.

However there still exists a need for pant type absorbent articles having a chassis region comprising an elastic laminate having good strength properties, comfort, fit and soft feel as well as a cloth-like appearance. One problem occurring is that the elastic laminate breaks when the wearer or caregiver pulls up the pant.

OBJECT AND MOST IMPORTANT FEATURES OF THE INVENTION

The object of the present invention is to provide a pant type absorbent article having a core region and a chassis region and which combines strength properties with comfort and fit to the wearer's body, a soft and cloth-like appearance and feel close to textile materials.

The pant type absorbent article according to the invention has a core region comprising an absorbent core and a chassis region surrounding the core region, said chassis region comprising front, back and waist regions, while the core region is located at least in the crotch portion of the article, a liquid impermeable backsheet is arranged at least in the core region on the garment facing side of the absorbent core and a liquid permeable topsheet is arranged at least in the core region on the wearer-facing side of the absorbent core. In at least a part of the chassis region the article comprises a coversheet in the form of an elastic laminate composed of at least two web shaped material layers in the form of nonwoven and/or film layers, at least one of said web shaped materials being an elastic material, said elastic laminate material constituting the sole component of the chassis in at least 20% of the total surface area of the article, said elastic web material having:
  a) a tensile strength of at least 15 N/25 mm both in the longitudinal (y) and the transverse (x) direction of the article;
  b) a tensile strength in transverse direction (x) of the article which is no more than 2.5 times and preferably no more than 2 times higher than the tensile strength in the longitudinal direction (y) of the article; and
  c) wherein the force required to extend the elastic laminate 10% in the longitudinal direction (y) of the article is no more than 5 N/25 mm as measured by the Tensile Strength test method disclosed herein.

By adapting the tensile strength properties as well as the required force to extend the laminate 10% in the longitudinal direction of the article to the needs and the actual forces exerted to the pant in the different directions thereof during normal use and especially when taking on and pulling up the pant, the materials comprised in the laminate can be chosen in a cost efficient manner and with regard to both the required strength properties as well as comfort and textile feel.

Preferably said elastic laminate material has a basis weight of no more than 120 g/m$^2$, preferably no more than 110 g/m$^2$ and more preferably no more than 100 g/m$^2$.

In a further aspect the elastic laminate material has a tensile strength of at least 20 N/25 mm both in the longitudinal (y) and the transverse (x) direction of the article.

In a still further aspect the force required to extend the elastic laminate 10% in the longitudinal direction (y) of the article is no more than 4 N/25 mm and preferably no more than 3 N/25 mm as measured by the Tensile Strength test method.

In one embodiment the elastic laminate is composed of first and second layers of fibrous material and an elastic film layer located between said first and second fibrous layers, In one aspect of the invention at least one of the layers of fibrous material is a creped nonwoven material.

In a further aspect the first layer of fibrous material and the elastic film layer form parts of a first elastic laminate that has been rendered elastic by incremental stretching and partial tearing of the first layer of fibrous material and in that said first elastic laminate has been bonded to the second layer of fibrous material while in a stretched state, whereby the laminate is elastically stretchable.

In a still further aspect the first layer and second layers of fibrous material have been bonded to the elastic film layer while this is in a stretched state, whereby the laminate is elastically stretchable.

In one embodiment the elastic laminate material has an elasticity in the transverse direction (x) of the article of at least 30%, preferably at least 50%, more preferably 70%, when measured according to the Elasticity Test specified in the description.

In a further embodiment the elastic laminate material is non-elastic and extendible in the longitudinal direction (y) of the article and has a permanent deformation of more than 10% after having been stretched to a stretched width which is 30% greater than the original unstretched width according to the Elasticity Test described herein.

In a further embodiment at least one of the layers of fibrous material has an elongation at maximum load greater than the elasticity of the elastic laminate. It is preferred that both layers of fibrous material have an elongation at maximum load greater than the elasticity of the elastic laminate.

According to one aspect of the invention at least one of the layers of fibrous material have an elongation at maximum load of at least 10%, preferably at least 20% greater than the elasticity of the elastic laminate.

It is preferred that said elastic film layer is breathable and that the elastic laminate has a Water Vapour Transmission Rate according to ASTM E96-00 Procedure D of at least 1500 $g/m^2$ 24 h, preferably at least 3000 $g/m^2$ 24 h. Preferably the elastic film layer has an open area of at least 5%, preferably at least 8%.

In one embodiment the first and/or the second layers of fibrous material comprise a mixture of polypropylene and polyethylene polymers.

In a further embodiment said elastic laminate comprises first and second fibrous layers of spunbond material, each having a basis weight of between 10 and 35 $g/m^2$, preferably between 12 and 30 $g/m^2$, more preferably between 15 and 25 $g/m^2$ and a breathable elastic film layer having a basis weight between 20 and 80 $g/m^2$, preferably between 20 and 60 $g/m^2$, said elastic laminate having a Water Vapour Transmission Rate according to ASTM E96-00 Procedure D of at least 1500 $g/m^2$ 24 h, preferably at least 3000 $g/m^2$ 24 h.

According to one aspect of the invention the elastic laminate constitutes the sole component of the chassis in at least 25%, preferably at least 30%, more preferably at least 40%, of the total surface area of the article.

According to a further aspect the elastic laminate has Softness (S) according to Kawabata of at least 20, preferably at least 30 and more preferably at least 40. It may further have a Formability (F) according to Kawabata of no more than 50, preferably no more than 30, more preferably no more than 20 and most preferably no more than 10. It may also have a Drapability (D) according to Kawabata of no more than 40.

In one embodiment a substantial part of the crotch portion of the article is free from said elastic laminate. For certain applications it is preferred that the waist region of the chassis is free from said elastic laminate.

Figure 2:
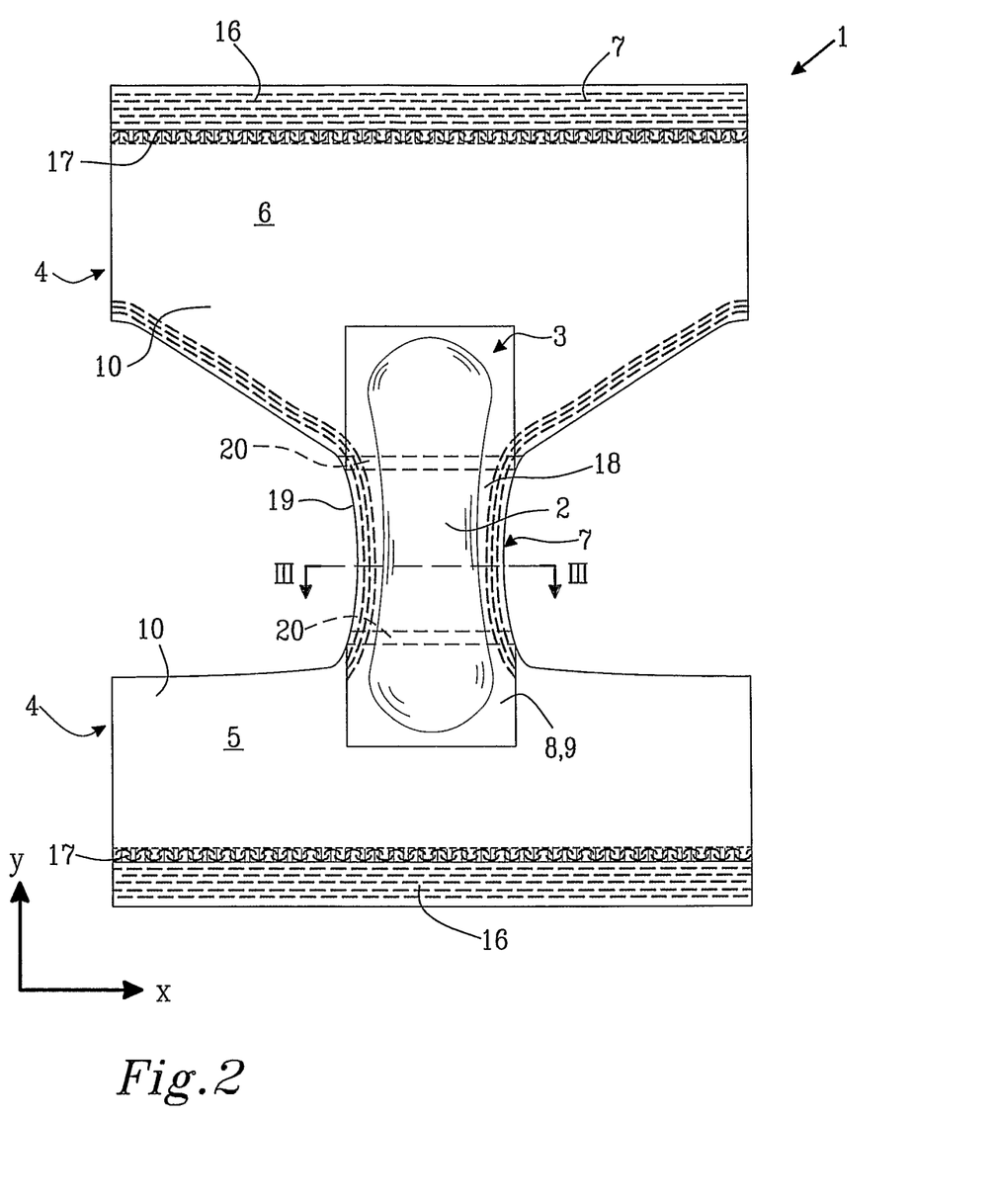
FIG. 2 shows is a simplified plan view of the pant article in its flat, uncontracted state prior to formation as seen from the body facing side.
Figure 3:
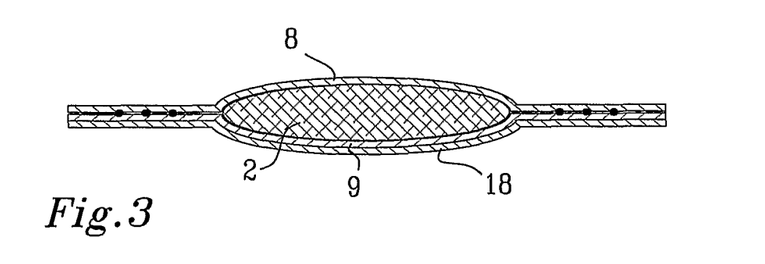
FIG. 3 is a cross section according to the line III-III in FIG. 2.
Figure 4:
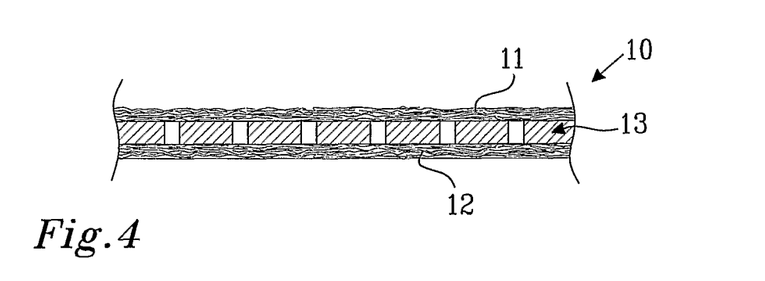
FIG. 4 is a cross section through an elastic laminate according to the invention.

According to one embodiment the surface area of the absorbent core amounts to no more than 30%, preferably not more than 20%, of the total surface area of the article, as measured in a flat state of the article. The term "flat state" herein means in an opened untensioned state, as seen in FIG. 2 of the drawings, and in which any tensioned elastic members have been deactivated.

In a further aspect of the invention the article is a "pull-up" pant diaper product comprising an elastic waist region, which is free from said elastic laminate, a crotch portion which is also free from said elastic laminate and wherein the elastic web material is arranged as the sole component in at least a substantial part of the front region of the article, which in use is intended to be applied over the stomach of the wearer. The term "a substantial part" herein means at least 50% of the surface area of the front region.

DESCRIPTION OF PREFERRED EMBODIMENTS

The invention will in the following be closer described with reference to some embodiments shown in the accompanying drawings.

Absorbent Article

The term "absorbent article" refers to products that are placed against the skin of the wearer to absorb and contain body exudates, like urine, feces and menstrual fluid. The invention mainly refers to disposable absorbent articles, which means articles that are not intended to be laundered or otherwise restored or reused as an absorbent article after use. According to the invention pant type absorbent articles are referred to having a core region and a chassis region surrounding the core region. Examples of such pant type absorbent articles are pant diapers, sanitary pants and incontinence pants.

The drawings show an embodiment of a pant diaper 1 for an infant or an incontinent adult. Said pant diaper typically comprises an absorbent core 2 located in a core region 3 of the article, and a chassis 4 surrounding the core region. The chassis comprises front 5, back 6 and waist regions 7. The core region 3 is located at least in the crotch portion 19 of the article and extends a certain distance into the front 5 and back regions 6. The crotch portion 19 is herewith defined as the narrow part of the article intended to be worn in the wearer's crotch between the legs.

The article has a longitudinal direction y and a transverse direction x.

The article comprises a liquid permeable topsheet 8 and a liquid impermeable backsheet 9 covering at least the core region 3. The absorbent core 2 is enclosed between the topsheet and the backsheet.

Topsheet

The liquid permeable topsheet 8 can consist of a nonwoven material, e g spunbond, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and intended to be readily penetrated by body fluid, e.g. urine or menstrual fluid. The topsheet may be different in different parts of the absorbent article.

Backsheet

The liquid impervious backsheet 9 covering the core region 3 on the garment-facing side of the core is of a liquid impervious material, such as a thin plastic film, e.g. a polyethylene or polypropylene film, a nonwoven material coated with a liquid impervious material, a hydrophobic nonwoven material, which resists liquid penetration or a laminate comprising plastic films and nonwoven materials. The core region backsheet material 9 may be breathable so as to allow vapour to escape from the absorbent core, while still preventing liquids from passing therethrough. Examples of breathable backsheet materials are porous polymeric films, nonwoven laminates from spunbond and meltblown layers, laminates from porous polymeric films and nonwovens. The backsheet 9 is preferably inelastic.

Absorbent Core

The absorbent core 2 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body it is also common to have absorbent bodies comprising layers of different material with different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent. The size and absorbent capacity of the absorbent core may be varied to be suited for different uses such as for infants or for incontinent adults.

Coversheet

The coversheet 10 covering the front and back regions 5 and 6 of the chassis 4 comprises an elastic laminate material having a basis weight of no more than 100 g/m$^2$. The elastic laminate material 10 is elastic at least in the transverse x-direction of the article. The elasticity in the x-direction should be at least 30%, preferably at least 50%, more preferably at least 70%, as measured by the Elasticity Test specified below.

Preferably the laminate 10 is non-elastic and extendible in the longitudinal y-direction of the article. "Extendible" means that it can be stretched to a stretched width which is at least 30% greater than the original stretched width and has a permanent deformation of more than 10% upon relaxation of the stretching force after 60 seconds.

The elastic laminate 10 according to the invention is composed of at least two web-shaped material layers in the form of nonwoven layers and/or film layers. At least one of the layers is elastic, wherein said elastic layer is a web shaped material, such as a nonwoven or a film. Thus laminates in which elongated elastic members, such as elastic threads or strips, are contractably affixed in an extended state between web-shaped materials, for example nonwoven materials, are not included. In the embodiment shown and described below the elastic laminate 10 is composed of first and second outer layers of fibrous material 11 and 12 and a middle elastic film layer 13 located between said fibrous layers.

In the elastic laminate shown and described below it is preferred that the outer fibrous layers 11 and 12 are chosen so that they, in combination with the inner elastic film layer, give the material high resistance to puncture and a tensile strength of at least 15 N/25 mm and preferably at least 20 N/25 mm both in the longitudinal, y, and the transverse, x, direction of the article. The elastic laminate material further should have a tensile strength in transverse direction, x, of the article which is no more than 2.5 times and preferably no more than 2 times higher than the tensile strength in the longitudinal direction, y, of the article. They also provide a soft and cloth-like feel to the laminate. Examples of suitable materials used as outer fibrous layers 11, 12 are carded webs, spunbond materials and creped or creased nonwovens. The basis weight of the fibrous material layers should be between 10 and 35 g/m$^2$, preferably between 12 and 30 g/m$^2$, more preferably between 15 and 25 g/m$^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and through this, give the nonwoven material a higher elongation at maximum load. A mixture of polyethylene and polypropylene polymers has proved to provide good results in this respect. A mixture of fibers of different polymers is also possible.

Figure 5:
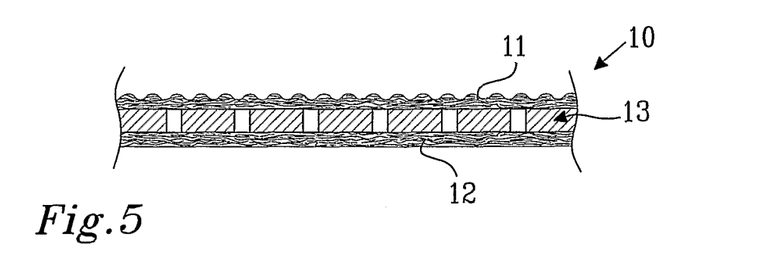
FIG. 5 is a cross section through another embodiment of an elastic laminate according to the invention.

In one embodiment shown in FIG. 5 at least one of the layers of fibrous layers 11 is a creped nonwoven material. The creped nonwoven will increase the puncture resistance of the laminate puncture resistant and allow it to be subjected to the pulling and stretching forces that occur when putting on and taking off the pant article without breaking and tearing.

The middle layer is according to one embodiment of the invention an apertured elastic film having a basis weight between 20 and 80 g/m$^2$, preferably between 20 and 60 g/m$^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

The total basis weight of the laminate is preferably 120 g/m$^2$ or less, preferably no more than 110 g/m$^2$ and more preferably no more than 100 g/m$^2$.

The elastic laminate 10 may be manufactured according to the method disclosed in WO 03/047488, wherein one spunbond layer 11 is applied to the film 13 in a tacky state and will thus bond to the film layer, while the other spunbond layer 12 is adhesively laminated to the film layer 13, using for example a pressure sensitive hot melt adhesive. Alternatively the laminate is manufactured according to a modified version of this known method, wherein the modification involves that the laminate is incrementally stretched (through intermeshing gears, IMG), to a point below the elongation at peak load of at least one of the non-elastic nonwoven layers to retain some strength for at least one of the nonwoven layers. The other layer may also be stretched to a point below its elongation at peak load, or to a point at which it will tear during stretching.

The method disclosed in WO 03/047488 involves stretching of the laminate above the point of failure of the fibrous material, so that the non-elastic layers break completely.

Therefore, as described in WO 03/047488, the elongation of the laminate is not limited by the stretch modulus of the non-elastic material.

According to the modified method at least one, preferably both fibrous layers, which are bonded to the elastic film are not, in contrast to the method described in WO 03/047488, completely torn upon manufacture of a laminate according to the present invention. Selection of fibrous materials which have an elongation at maximum load greater than the elasticity of the elastic laminate allows the elastic film to stretch without being hindered by the fibrous layers. Such a selection also ensures that the fibrous layers contribute to the puncture resistance of the laminate, as they are not completely torn or broken during manufacture. Preferably the fibrous layers, or at least one of the fibrous layers have an elongation at maximum load that is at least 10% higher than the elasticity of the laminate. This is described in more detail in PCT/SE2004/001005, which is incorporated herein by reference.

In an alternative embodiment the laminate 10 is manufacture by feeding a first fibrous layer in the form of a nonwoven web into a bonding nip and extruding a molten elastic film-forming polymer through a die into the nip. The first fibrous layer and the elastic film form a first laminate. In a second lamination step the film side of the first laminate is coated or sprayed with adhesive and is subsequently passed through a second bonding nip together with a second fibrous layer to form the laminate 10. The laminate is subsequently activated by subjecting it to incremental stretching by passing it through intermeshing gears, IMG.

In a further embodiment the first layer of fibrous material 11 and the elastic film layer 13 form parts of a first elastic laminate that has been rendered elastic by incremental stretching and partial tearing of the first layer of fibrous material 11 and in which the first elastic laminate has been bonded to the second layer of fibrous material 12 while in a stretched state. The resulting the laminate will then be elastically stretchable.

In a still further embodiment the first and second layers of fibrous material have been bonded to the elastic film layer while this is in a stretched state. The resulting laminate will be elastically stretchable.

The opacity of a material layer is the characteristic ability of the material layer to visually hide from view an underlying object or pattern. The opacity is measured in %, wherein 100% opacity means that nothing can be seen through the material layer and 0% means that the material layer is completely transparent. The opacity is measured by the Opacity Test described below, which is based on luminous-reflectance-factor data.

Opacity of the laminate can be obtained by the incorporation of opacifying fillers into the laminate, particularly into the elastic film. Such pigments can be organic or inorganic dyes, colouring agents, or whitening agents. Inorganic materials such as titanium dioxide, inorganic carbonates, synthetic carbonates, talc, nepheline syenite, magnesium hydroxide, aluminium trihydrate siatomaceous earth, mica, natural or synthetic silicas, calcinated clays and mixtures thereof are preferred examples of opacifying fillers.

The filler is preferably added as a master batch at the extrusion of the film. One example of an appropriate concentration is about 5% filler by weight of the film.

It is further preferred that the elastic laminate 11 has a breathability (Water Vapour Transmission Rate) according to ASTM E96-00 Procedure D of at least 1500 g/m$^2$ 24 h, preferably at least 3000 g/m$^2$ 24 h.

The open area of the elastic film layer is preferably at least 5%, more preferably at least 8%. The open area is measured by image analysis methods and is defined as the sum of the hole area divided by the total area of the film sample.

The elastic laminate according to the invention should have a tensile strength of at least 15 N/25 mm, preferably at least 20 N/25 mm both in the longitudinal (y) and the transverse (x) direction of the article. It should further have a tensile strength in transverse direction (x) of the article which is no more than 2.5 times and preferably no more than 2 times higher than the tensile strength in the longitudinal direction (y) of the article.

It has according to the invention been found that the above tensile strength properties are well adapted to the needs and the actual forces exerted to the pant in the different directions thereof during normal use and especially when taking on and pulling up the pant. The tensile strength properties need not be oversized in the transverse x-direction of the article relative to the tensile strength properties in the longitudinal y-direction. This means that the materials comprised in the laminate can be chosen in a cost efficient manner and with regard to both the required strength properties as well as to comfort and textile feel.

The force required to initially extend the laminate in longitudinal direction (y) of the article 10% of its unstretched length should further be low and no more than 5 N/25 mm, preferably no more than 4 N/25 mm and more preferably no more than 3 N/25 mm. This will make the pant easier to pull up and provides an improved fit and comfort. The force is measured according to the Tensile Strength test described below.

Figure 6:
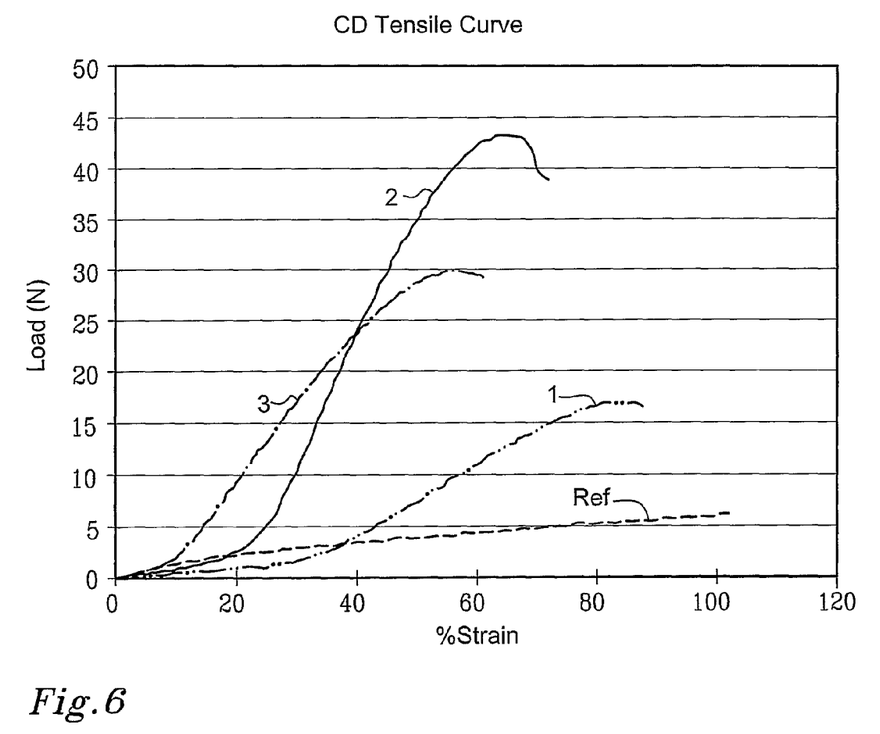
FIG. 6 are graphs showing tensile curves for a number of elastic laminates.

FIG. 6 shows tensile curves for a number of different laminates of the force required to stretch (expand) the laminate to different degrees. The graphs are referred to as "CD tensile curves" since the laminates were tested in their CD (cross machine direction), which in the pant article becomes the longitudinal direction, y. According to the invention it is desired that a relatively low force should be required to initially expand (stretch) the laminate up to 10% strain.

The following materials were tested:

Reference, Flexair 402, which is a conventional activated three-layer laminate comprising an inner apertured styrene based elastic film, basis weight 40 g/m$^2$ and two outer layers of PP (polypropylene) spunbond materials, each having a basis weight of 25 g/m$^2$. The laminate was made by bonding the spunbond layers to the elastic film and subsequently incrementally stretching (activating) the laminate, at which the non-elastic spunbond materials were stretched to a point below the elongation at maximum load to retain some strength in the spunbond layers. The material is produced by Tredagar under the trade name "Flexaire 402". The basis weights of the layers refer to the basis weight of the individual layers before activation.

Sample 1, which is a three-layer laminate comprising a first activated bi-laminate comprising a PP spunbond layer having a basis weight of 25 g/m$^2$ (BBA Sofspan 200) and an apertured styrene based elastic film, basis weight 40 g/m$^2$ that has been further laminated under stretching by 100% with a PP spunbond layer having a basis weight of 15 g/m$^2$ (BBA 044SSLP0090).

Sample 2, which is a three-layer laminate comprising an activated olefin/styrene based elastic film, basis weight 35 g/m$^2$ that has been laminated under stretching by 110% with two PP spunbond layers each having a basis weight of 15 g/m$^2$ (BBA 044SSLPO090).

Sample 3, which is a three-layer laminate comprising a first activated bi-laminate comprising a PP spunbond layer having a basis weight of 25 g/m$^2$ (BBA Sofspan 200) and an apertured styrene based elastic film, basis weight 40 g/m$^2$, that has been further laminated under stretching by 100% with a PP spunbond layer having a basis weight of 20 g/m² (Avgol SBPP N20-020-26).

The test results are shown in Table 1 below.

TABLE 1

| Sample | Tensile strength MD N/25 mm | Tensile strength CD N/25 mm | Tensile strength ratio MD/CD | Force (N/25 mm) at 10% extension in CD |
|---|---|---|---|---|
| Ref. | 34 | 10 | 3.4 | 1.6 |
| 1 | 25 | 18 | 1.4 | 0.5 |
| 2 | 31 | 44 | 0.7 | 0.9 |
| 3 | 27 | 30 | 0.9 | 2.2 |

Samples 1, 2 and 3 all fulfil the requirements according to the present invention of having a tensile strength of at least 15 N/25 mm in both MD and CD, a tensile strength ratio MD/CD of no more than 2.5 and a force of no more than 5 N/25 mm for extending the material in CD 10%.

Since the tested laminates are elastic mainly in the MD they are intended to be used in the absorbent article with the MD oriented in transverse direction, x, of the article and their CD oriented in the longitudinal direction, y, of the article.

Pant Article

Figure 1:
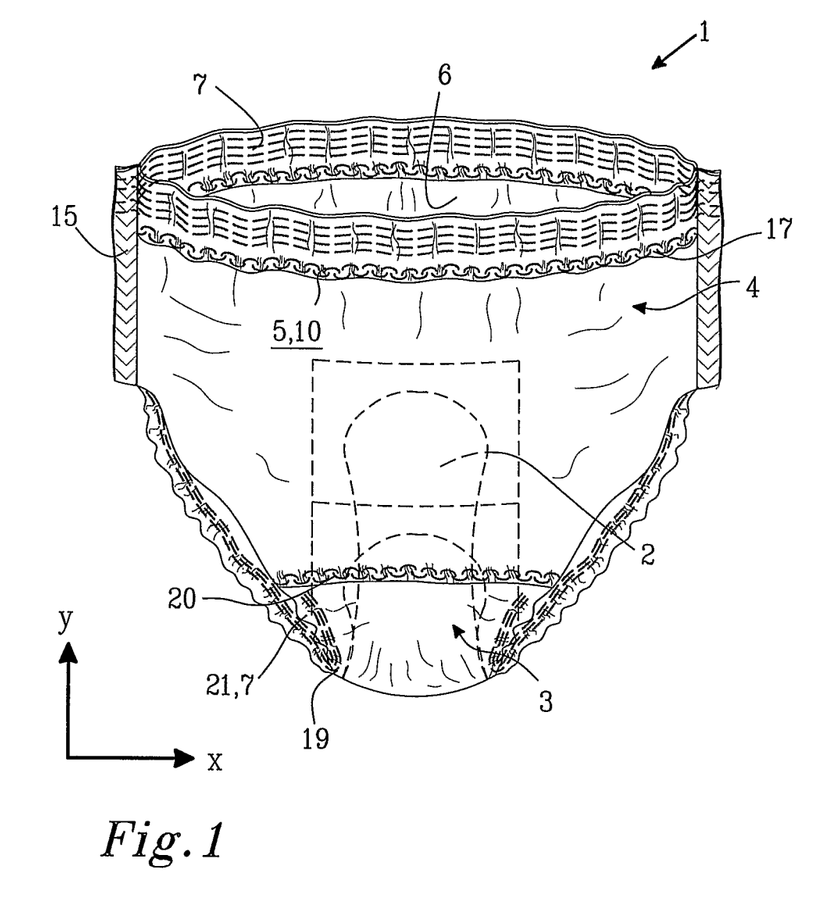
FIG. 1 shows a perspective view of a "pull-up" pant article.

The pant article disclosed in FIG. 1 is intended to enclose the lower part of the wearer's trunk like a pair of absorbent pants. It comprises a core region 3 located in the narrow crotch portion 19 of the article and extending into the front 5 and back regions 6 of the absorbent pants. A chassis region 4 surrounds the core region 3. The core region 3 is defined as the surface area of the article which is occupied by the absorbent core 2 and the areas outside the core which are covered by the liquid-impervious backsheet 9. The chassis 4 comprises front 5, back 6 and waist regions 7 located outside the crotch region 3. The front 5 and back regions 6 are joined to each other along their longitudinal edges by ultrasonic welds 15, glue strings or the like.

According to one embodiment of the invention the surface area of the absorbent core 2 amounts to no more than 30% of the total surface area of the article, preferably no more than 20%, as measured in a flat state of the article. The term "flat state" herein means in an opened untensioned state, as seen in FIG. 2, and in which any tensioned elastic members have been deactivated.

The elastic laminate material 10 may cover the entire article, including the core region 3 and the entire chassis region 4. However according to a preferred embodiment a substantial part of the crotch portion 19 of the article is free from the elastic laminate material 10. A "substantial part" used herein refers to at least 50%, preferably at least 75%. Preferably also the waist region 7 of the chassis region is free from the elastic laminate material 10. The waist region 7 comprises a nonwoven material that is elasticized by elastic members 16, such as elastic threads, contractably affixed between material layers, such as nonwoven materials. Such elastic members may also be arranged around the leg openings of the article. Ultrasonic welds 17, glue strings or the like, join the elastic laminate 10 to the elasticized nonwoven in the waist region 7.

The liquid-impervious backsheet material 9 underlies the absorbent core 2 and adjacent areas immediately outside the absorbent core 2. The area covered by the liquid-impervious backsheet 9 is defined as the core region 3. A nonwoven material 18 is arranged on the garment-facing side of the liquid-impervious backsheet 9 in the crotch portion of the article. The nonwoven material 18 is joined to the elastic laminate material 10 by means of ultrasonic welds 20, glue strings or the like. The elastic laminate material 10 and the liquid impervious backsheet 9 overlap in the outer parts of the core region 3, wherein the elastic laminate material 10 is arranged on the garment facing side of the liquid impervious backsheet 9.

The elastic laminate material 11 is preferably arranged as an outside coversheet material as well as inner coversheet material over at least a substantial part of the front region 5 of the chassis 4, which during use is intended to be applied against the stomach of the wearer, except for the waist region 7. A "substantial part" used herein means at least 50% of the surface area, preferably at least 75%, of the surface area of the front region 5 of the chassis 4. It is further preferred that the elastic web material 10 is arranged as an outside coversheet material as well as inner coversheet material over both the front 5 and back regions 6 of the chassis 4. Thus no additional backsheet or topsheet materials are required and the elastic web material constitutes the sole component of in these parts of the chassis 4. In at least 20%, preferably at least 25%, more preferably at least 30% and most preferably at least 40% of the total surface area of the article, as seen in a flat state according to FIG. 2, the elastic laminate material 10 constitutes the sole component of the chassis.

No additional elasticized side panels joining the front and back regions 5 and 6 are needed when using the elastic laminate material 10 according to the invention. If desired, additional elasticized side panels may of course be provided, especially in cases where the elastic laminate material 10 is arranged only in parts of the front and/or back regions.

As stated above the elastic laminate material 10 has an opacity of at least 40%, preferably at least 50% and more preferably at least 60%.

The opacity of the elastic web material provides a cloth-like appearance to the article, which is of particular importance when the article is a pant diaper. Especially in this case, where the elastic web material forms the sole component in considerable surface area regions of the pant diaper, such as large areas of the front and back regions, and the absorbent core covers only relatively small areas, 30% or less, of the article, the appearance of the elastic web material is of great importance for the overall appearance of the article. Thus by making the elastic web material opaque with an opacity of at least 40%, the pant diaper will appear more cloth-like and more like "normal" underwear, than if the elastic web material would have a higher degree of transparency.

It is further desired that the elastic web material has a puncture resistance of at least 15 N as measured according to ASTM Designation D3763-02. Preferably, the elastic web material of the present invention has a puncture resistance of at least 20 N, and more preferably at least 30 N.

The elastic web material should preferably have a softness according to Kawabata of at least 20, preferably at least 30 and most preferably at least 40.

It is further desired that it has a formability according to Kawabata of no more than 50, preferably no more than 30, more preferably no more than 20 and most preferably no more than 10.

It is also desired that the elastic web material has a drapability according to Kawabata of no more than 40.

Description of Test Methods

Opacity

The opacity of the elastic web material is measured according to a slightly modified version of SS-ISO 2471:1998 by Swedish Standard Institute (Diffuse Reflectance Method). The method is originally intended for measuring the opacity for paper sheets, but it also functions well for measuring the opacity of other types of sheet materials, such as elastic laminates according to this invention. The opacity is measured in an unstretched condition of the elastic web material. The principle of the test method is to measure the Single-Sheet Luminous Reflectance Factor, $R_0$, through a single sheet against a standardized black backing and the Intrinsic Luminous Reflectance Factor, $R_\infty$, against a completely opaque white backing. The opacity (%) is calculated from the formula $100 \cdot R_0/R_\infty$.

The following modifications of the test method were made:
i) When measuring the Single-Sheet Luminous Reflectance Factor, $R_0$, a black velvet fabric was used as backing.
ii) When measuring the Intrinsic Luminous Reflectance Factor, $R_\infty$, the measurement was made on one single sheet of the elastic laminate against a white tile as backing.
iii) The CIE illuminant D65 (10°) was used instead of the CIE illuminant C (2°).

The measured opacity values are mean values from five measurements.

Puncture Strength

Puncture strength is measured according to ASTM Designation D3763-02. From penetration impact-type tests, this method produces data of load versus displacement. The maximum load for each laminate is calculated.

Tensile Strength (Reference: ASTM D 882)

The method measures tensile strength and elongation of difference elastic materials. The tensile strength and elongation of a well-defined test piece is tested by means of a tensile tester.

Apparatus: Instron 4301
Tensile tester connected to a computer
Crosshead speed: 500 mm/min
Clamp distance: 50 mm
Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4h in 50% RH±5% RH and 23° C. ±2° C. before testing.

Procedure: The tensile tester is calibrated according to the apparatus instructions and set to zero. The sample is mounted and it is ensured that it is not obliquely or unevenly fastened. The material is prevented from slipping by using clamps covered with galloon or similar material. The tensile tester is started, and stopped after the material has broken (if not automatically controlled). Measurements resulting from premature failures (i.e. the sample breaks at the clamp, or is damaged during preparation) are ignored if possible.

The following results are expressed by the tensile tester/computer:
Maximum force, N/25.4 mm
Elongation at maximum force, %
Force required to extend the elastic laminate 10%, N/25 mm
Break force, N/25.4 mm
Elongation at break force, %
Knee point, N/%

Elasticity Test

The method measures how an elastic material behaves at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample is centred and fastened perpendicularly in the clamps. The tensile tester is started and three cycles between 0 and the predetermined elongation, equal to the highest defined $1^{st}$ load, are performed. Before the last cycle, the sample is relaxed for 1 minute, then the permanent elongation is measured by stretching the sample until a force of 0.1 N is detected and the elongation is read.

The permanent elongation after relaxation should be less than 10% and is measured by the method above. Thus an elasticity of 30% is defined as that the laminate should have a permanent relaxation after elongation of less than 10% after being exerted to an elongation of 30% in the tensile tester above. An elongation of 30% means an elongation to a length that is 30% longer than the initial length of the sample.

A non-elastic material is defined as a material having a permanent elongation after relaxation of more than 10% after having been subjected to an elongation of 30%.

Kawabata Tests

The Kawabata KES-FB test is a Japanese quality judgment system used for textile materials and is disclosed in "The Standardization and Analysis of Hand Evaluation (2nd Edition), Sueo Kawabata, July 1980, The Hand Evaluation and Standardization Committee, The Textile Machinery Society of Japan". The test used in this invention uses two of the Kawabata testing machines, KES-FB2 for measuring Bending rigidity, B (gf·cm$^2$/cm), and KES-FB1 for measuring Shear stiffness, G (gf/cm·degree) and Tensile strain, EMT (%).

Bending Rigidity (B) KES-FB2

The slope was measured between 0.5 cm$^{-1}$ and 1.5 cm$^{-1}$ and −0.5 cm$^{-1}$ and −1.5 cm$^{-1}$.

The measurements were performed in both directions (MD and CD) with the following settings:
Total sample area: 20×20 cm;
Maximum curvature: Kmax=±2.5 cm$^{-1}$;
Bending rate: 0.5 cm$^{-1}$/sec;
Sample effective dimension: 20 cm length and 1 cm width;
Bending deformation is applied to the width direction.

Shear Stiffness (G) KES-FB1

The slope was measured between 0.5 cm$^{-1}$ and 2.5 cm$^{-1}$ and −0.5 cm$^{-1}$ and −2.5 cm$^{-1}$.

The measurements were performed in both directions (MD and CD) with the following settings:
Total sample area: 20×20 cm;
Tension of specimen: W=W=10 gf/cm;
Maximum shear angle: $\phi=\pm 8°$.
Sample effective dimension: 20 cm width and 5 cm length;
Shear deformation is applied to the width direction.

Tensile Strain (EMT)

The measurements were performed in both directions (MD and CD) with the following settings:

Total sample area: 20×20 cm;
Maximum load: Fm=500 gf/cm;
Tensile speed: 0.2 mm/sec.
Sample effective dimension: 20 cm width and 2.5 cm length;
Tensile deformation is applied to the length direction.
Elongation sens 50 mm/10V.

Softness (S)

The Softness (S) according to Kawabata is obtained from the formula:

$$S=\sqrt{EMT/B}$$

Formability (F)

The Formability (F) according to Kawabata is obtained from the formula:

$$F=B \cdot EMT.$$

Drapability (D)

The Drapability (D) according to Kawabata is obtained from the formula:

$$D=116+25 \cdot \log(B \cdot G/W), \text{ wherein W is the basis weight of the sample.}$$

As described above it is further understood that other types of elastic web materials, than the laminate described above, may be used, such as elastic nonwoven materials, nonwoven materials which per se are inelastic, but which have been elastified by means of elastic threads etc. The elastic web materials may comprise one layer or two or more layers that have been laminated.

The invention claimed is:

1. A pant absorbent article, said article having a core region comprising an absorbent core and a chassis surrounding the core region, said chassis comprising front, back and waist regions, wherein the core region is located at least in a crotch portion of the article, a liquid impermeable backsheet is arranged at least in the core region on the garment-facing side of the absorbent core and a liquid permeable topsheet is arranged at least in the core region on the wearer-facing side of the absorbent core, said article having a longitudinal direction and a transverse direction, wherein said article in at least a part of the chassis region comprises a coversheet in the form of an elastic laminate comprising a first non-elastic non-woven web, a second non-elastic non-woven web and a web shaped elastic film layer between the first and second non-woven webs, said elastic laminate constituting the sole component of the chassis in at least 20% of the total surface area of the article, said elastic laminate having:

a) a tensile strength of at least 15 N/25 mm both in the longitudinal and transverse directions of the article as measured by the Tensile Strength test method disclosed in the specification;

b) a tensile strength in the transverse direction of the article which is no more than 2.5 times higher than the tensile strength in the longitudinal direction of the article as measured by the Tensile Strength test method disclosed in the specification; and c) wherein the force required to extend the elastic laminate 10% in the longitudinal direction of the article is no more than 5 N/25 mm as measured by the Tensile Strength test method disclosed in the specification, wherein of the first and second non-elastic non-woven webs, only the first non-elastic non-woven web has been partially torn and stretched, and the elastic laminate is elastic in a first direction, said first and second non-elastic non-woven webs each have a basis weight of between 10 and 35 g/m² and, and said elastic film layer has a basis weight between 20 and 80 g/m², and the first non-elastic non-woven web and the elastic film layer form parts of a first elastic laminate that has been rendered elastic by incremental stretching and partial tearing of the first non-elastic non-woven web and wherein said first elastic laminate has been bonded to the second non-elastic non-woven web while in a stretched state, whereby the elastic laminate is elastically stretchable.

2. The absorbent article as claimed in claim 1, wherein said elastic laminate as a whole has a basis weight no less than 50 g/m² and no more than 120 g/m².

3. The absorbent article as claimed in claim 2, wherein the elastic laminate as a whole has a basis weight of no more than 100 g/m².

4. The absorbent article as claimed in claim 1, wherein said elastic laminate has a tensile strength of at least 20 N/25 mm both in the longitudinal and transverse directions of the article.

5. The absorbent article as claimed in claim 1, wherein the force required to extend the elastic laminate 10% in the longitudinal direction of the article is no more than 4 N/25 mm as measured by the Tensile Strength test method disclosed in the specification.

6. The absorbent article as claimed in claim 5, wherein the force required to extend the elastic laminate 10% in the longitudinal direction of the article is not more than 3 N/25 mm.

7. The absorbent article as claimed in claim 1, wherein at least one of the first and second non-elastic non-woven webs is a creped nonwoven material.

8. The absorbent article as claimed in claim 1, wherein said elastic laminate has an elasticity in the transverse direction of the article of at least 30% when measured according to the Elasticity Test disclosed in the specification.

9. The absorbent article as claimed in claim 8, wherein the elastic laminate has an elasticity in the transverse direction of the article of at least 70%.

10. The absorbent article as claimed in claim 1, wherein said elastic laminate is non-elastic and extendible in the longitudinal direction of the article and has a permanent deformation of more than 10% after having been stretched to a stretched width which is 30% greater than the original unstretched width according to the Elasticity Test disclosed in the specification.

11. The absorbent article as claimed in claim 1, wherein at least one of the first and second non-elastic non-woven webs has an elongation at maximum load greater than the elasticity of the elastic laminate.

12. The absorbent article as claimed in claim 11, wherein at least one of the first and second non-elastic non-woven webs has an elongation at maximum load of at least 20% greater than the elasticity of the elastic laminate.

13. The absorbent article as claimed in claim 11, both first and second non-elastic non-woven webs have an elongation at maximum load greater than the elasticity of the elastic laminate.

14. The absorbent article as claimed in claim 11, wherein at least one of the first and second non-elastic non-woven webs have an elongation at maximum load of at least 10% greater than the elasticity of the elastic laminate.

15. The absorbent article as claimed in claim 1, wherein said elastic film layer is breathable.

16. The absorbent article as claimed in claim 15, wherein said elastic laminate has a Water Vapour Transmission Rate according to ASTM E96-00 Procedure D of at least 1500 g/m$^2$ 24 h.

17. The absorbent article as claimed in claim 16, wherein the elastic laminate has a Water Vapour Transmission Rate according to ASTM E96-00 Procedure D of at least 3000 g/m$^2$ 24 h.

18. The absorbent article as claimed in claim 15, wherein the elastic film layer has an open area of at least 5%.

19. The absorbent article as claimed in claim 18, wherein the elastic film layer has an open area of at least 8%.

20. The absorbent article as claimed in claim 1, wherein the first and/or the second non-elastic non-woven web comprises a mixture of polypropylene and polyethylene polymers.

21. The absorbent article as claimed in claim 1, said elastic laminate having a Water Vapour Transmission Rate according to ASTM E96-00 Procedure D of at least 1500 g/m$^2$ 24 h.

22. The absorbent article as claimed in claim 1, wherein the elastic laminate constitutes the sole component of the chassis in at least 25% of the total surface area of the article.

23. The absorbent article as claimed in claim 22, wherein the elastic laminate constitutes the sole component of the chassis in at least 40%, of the total surface area of the article.

24. The absorbent article as claimed in claim 1, wherein said elastic laminate has Softness according to Kawabata of at least 20.

25. The absorbent article as claimed in claim 24, wherein the elastic laminate has Softness according to Kawabata of at least 40.

26. The absorbent article as claimed in claim 1, wherein said elastic laminate has a Formability according to Kawabata of no more than 50.

27. The absorbent article as claimed in claim 26, wherein said elastic laminate has a Formability according to Kawabata of no more than 10.

28. The absorbent article as claimed in claim 1, wherein said elastic laminate has a Drapability according to Kawabata of no more than 40.

29. The absorbent article as claimed in claim 1, wherein a substantial part of the crotch portion of the article is free from said elastic laminate.

30. The absorbent article as claimed in claim 1, wherein the waist region of the chassis is free from said elastic laminate.

31. The absorbent article as claimed in claim 1, wherein the surface area of the absorbent core amounts to no more than 30% of the total surface area of the article, as measured in a flat state of the article.

32. The absorbent article as claimed in claim 31, wherein the surface area of the absorbent core amounts to no more than 20% of the total surface area of the article, as measured in a flat state of the article.

33. The absorbent article as claimed in claim 1, wherein the article is a pull-up pant product comprising an elasticized waist region, which is free from said elastic laminate, a crotch portion which is also free from said elastic laminate and wherein the elastic laminate is arranged as the sole component of the chassis in at least a substantial part of the front region of the chassis, which in use is intended to be applied over the stomach of the wearer.

34. The absorbent article as claimed in claim 1, wherein the article is a pant diaper, a sanitary pant or an incontinence pant.

35. The absorbent article as claimed in claim 1, wherein the tensile strength in the transverse direction of the article is no more than 2 times higher than the tensile strength in the longitudinal direction of the article.

36. The absorbent article as claimed in claim 1, wherein: (a) the first and second non-elastic non-woven webs each has a basis weight of between 15 and 25 g/m$^2$; (b) the elastic film layer has a basis weight between 20 and 60 g/m$^2$; or (c) the elastic laminate has a Water Vapour Transmission Rate of at least 3000 g/m$^2$ 24 h.

\* \* \* \* \*